United States Patent [19]

Lelong

[11] Patent Number: 4,699,886

[45] Date of Patent: Oct. 13, 1987

[54] METHOD OF PREPARING GAS SAMPLES FROM LIQUIDS INITIALLY CONTAINING SUCH GASES

[75] Inventor: Bernard Lelong, Arthez de Bearn, France

[73] Assignee: Societe Nationale Elf Aquitaine (Production), France

[21] Appl. No.: 860,019

[22] Filed: May 6, 1986

[30] Foreign Application Priority Data

May 7, 1985 [FR] France ................. 85 06951

[51] Int. Cl.⁴ .................. G01N 1/22; G01N 33/26
[52] U.S. Cl. .................. 436/60; 55/37; 55/53; 73/863.12; 73/863.21; 436/177; 436/181
[58] Field of Search ............ 73/863.12, 863.21; 55/37, 53; 436/177, 181, 178, 60, 68; 422/101

[56] References Cited

U.S. PATENT DOCUMENTS

| | | | |
|---|---|---|---|
| 2,489,893 | 11/1949 | Johnson | 73/863.21 |
| 2,703,015 | 3/1955 | Sykes | 73/863.21 |
| 3,556,730 | 1/1971 | Mitacek | 73/863.12 X |
| 4,131,437 | 12/1978 | Campbell et al. | 55/53 |
| 4,612,020 | 9/1986 | Fischer et al. | 55/53 X |

FOREIGN PATENT DOCUMENTS 0017106 10/1980 European Pat. Off.
56-158943 12/1981 Japan.

*Primary Examiner*—Barry S. Richman
*Assistant Examiner*—Robert J. Hill, Jr.
*Attorney, Agent, or Firm*—Ostrolenk, Faber, Gerb & Soffen

[57] ABSTRACT

A method is provided for continuous quantitative analysis of H₂S dissolved in crude oil. The liquid is injected into a mixing chamber 14 in the form of a microsprayed mist meeting a nitrogen stream. The mist conveyed by the nitrogen is injected in the lower unfilled part 16a of a mist separation chamber 16 filled with solid mist separation material and passes from bottom to top through said filling while giving up liquid in the form of coalesced droplets. The gas and nitrogen mixture emerging at the top 16b of chamber 16 is free of at least a large part of the least volatile constituents.

6 Claims, 2 Drawing Figures

METHOD OF PREPARING GAS SAMPLES FROM LIQUIDS INITIALLY CONTAINING SUCH GASES

The present invention relates to a method for the continuous preparation of gas samples from a liquid in which said gas is initially dissolved, consisting of filtering the liquid so as to free it of heavy constituents and impurities, expanding the liquid to a given pressure, injecting a given volume of the liquid into a nitrogen stream and conveying the sample thus prepared towards a gas analyzer. Such methods, more particularly for the quantitative analysis of $H_2S$ dissolved in crude oil, are known but have drawbacks. In fact, with these methods, the nitrogen conveying a given sample volume passes into a heat regulated extraction chamber where extraction of the $H_2S$ passing through the nitrogen stream takes place, with the gas free liquid dropping to the bottom of the extraction chamber. The $H_2S$ charged nitrogen is fed directly to an analyzer operating by photoelectric measurement of the blackening of paper impregnated with lead acetate. It has been proven that the extraction of $H_2S$ from the nitrogen stream is accompanied by droplets which are conveyed by the vector stream and cause fouling of the ducts, which requires frequent dismantling thereof for cleaning.

Filtering cartridges placed upstream of the volumetric device taking the oil sample, which cartridges alone provide filtering of the impurities, become rapidly clogged up and require the apparatus to be frequently dismantled to replace the filtering cartridges.

Finally, the volumetric sample taking device is a slide distributor driven with a reciprocal movement and comprises cylindrical channels, one of which forms the oil sample volume, which become fouled up and clogged up frequently, thus adversely affecting the good reproducibility of the measurement results.

The purpose of the present invention is to avoid these drawbacks by providing a sure and reliable operational conditioning method which may operate for long periods of time practically without interruption for dismantling and cleaning and which gives perfectly reproducible and reliable measurement results.

The method of the invention is characterized in that the liquid is injected into a mixing and extraction chamber in the form of a microsprayed mist meeting a nitrogen stream, which nitrogen stream serves as a vector gas. The mist carried by the nitrogen is then injected into the lower unfilled part of a mist separation chamber filled with solid mist separating material, with the lower unfilled part of the mist separation chamber serving as a rest chamber. The mist carried by the nitrogen then passes from bottom to top through said filling and given up liquid in the form of coalesced droplets during its passage through the filling. The mixture of gas, which is initially contained in the liquid and nitrogen, emerges at the top of the chamber and is free of at least a large part of the least volatile constituents of the liquid.

Thus, the oil sample, which is simply prefiltered by means of a cartridge filter, after expansion and volumetric quantitative analysis, is sprayed in the form of microdroplets, preferably by means of a nozzle of 0.5 to 0.7 mm in diameter, into the mixing chamber where it meets a nitrogen stream. The mist produced is fed into an extraction chamber in which the dissolved gas passes into the nitrogen phase, in the mist separation chamber thereof. The material filling this chamber may be formed by any aerosol separation material preferably by a material commercialized under the trademark B-GON by the firm SYMALIT. It is a structure of woven thermoplastic monofilaments in stacked layers which are capable of removing the aerosols whose droplet diameter may go down as far as 0.5 micron with a separation rate higher than 99.9%.

Thus, the purpose of creating the microsprayed mist is to extract all of the gas dissolved in the liquid into the nitrogen vector, thanks to a very large exchange area. The filling layer ensures a very thorough separation of gas exhausted droplets, so that the outgoing nitrogen transports practically only the initially dissolved gas which will be quantitatively analyzed in the analyzer. Another characteristic of the invention resides in the use of a displacement pump operating along the lines of a rotary piston which moves with a reciprocal translational movement inside a cylinder having liquid intake and discharge ports, said piston operating as a valve with respect to said ports. In fact, this kind of micropump, which is commercialized under the trademark FMI by the firm FLUID METERING INC., allows a very good reproducibility of the results to be obtained because of the self cleaning effect due to the rotary and reciprocal scavenging by the piston and a very accurate flow rate adjustment of the pumping capacity.

Preferably, the mixing chamber is connected to the mist separation chamber by a tube. The liquid mist conveyed by the nitrogen stream is fed through the tube to the lower part of the separation chamber while passing through the layer of mist separation material filling said chamber.

The assembly for conditioning the sample is situated in an enclosure whose temperature is controlled by thermostat to a temperature compatible with the characteristics of the liquid and the dissolved gas, for example varying between 40° and 70° C. for crude oil samples.

In a first variant, the mist separation chamber is place in a thermostat controlled enclosure whose temperature is kept between 40° and 70° C. and the gas mixture conveyed by a tube out of the enclosure passes through a second mist separation chamber placed at ambient temperature.

Thus, before being fed to the analyzer, the gas sample undergoes another operation for separating the liquid droplets which may have escaped the first separation operation carried out at the temperature of the thermostat controlled enclosure. The second operation takes place then in a separation chamber similar to the first one but operating at ambient temperature.

In a second variant, only the part of the separation chamber in which the mist is introduced is placed inside the thermostat controlled enclosure. The main body of the chamber, filled with mist separation material is placed at ambient temperature outside the thermostat controlled enclosure and its upper part is formed by an enclosure cooled to a temperature between +5° and +10° C. so that the constitutents of the mist leaving the mist separation material layer and having a condensation point greater than or equal to the ambient temperature are condensed and fall by gravity back onto said separation material layer.

The coalesced oil droplets preferably leave the separation chamber by a duct placed in the thermostat controlled enclosure and pass through a drainage lock chamber formed by two valves which have a capacity placed therebetween and which are actuated in turn by double acting pneumatic servo motors controlled by a clockwork mechanism.

BRIEF DESCRIPTION OF THE DRAWINGS

Other features of the method of the invention will be clear from the following description of variants given by way of examples and illustrated by the drawings in which.

Figure 1:
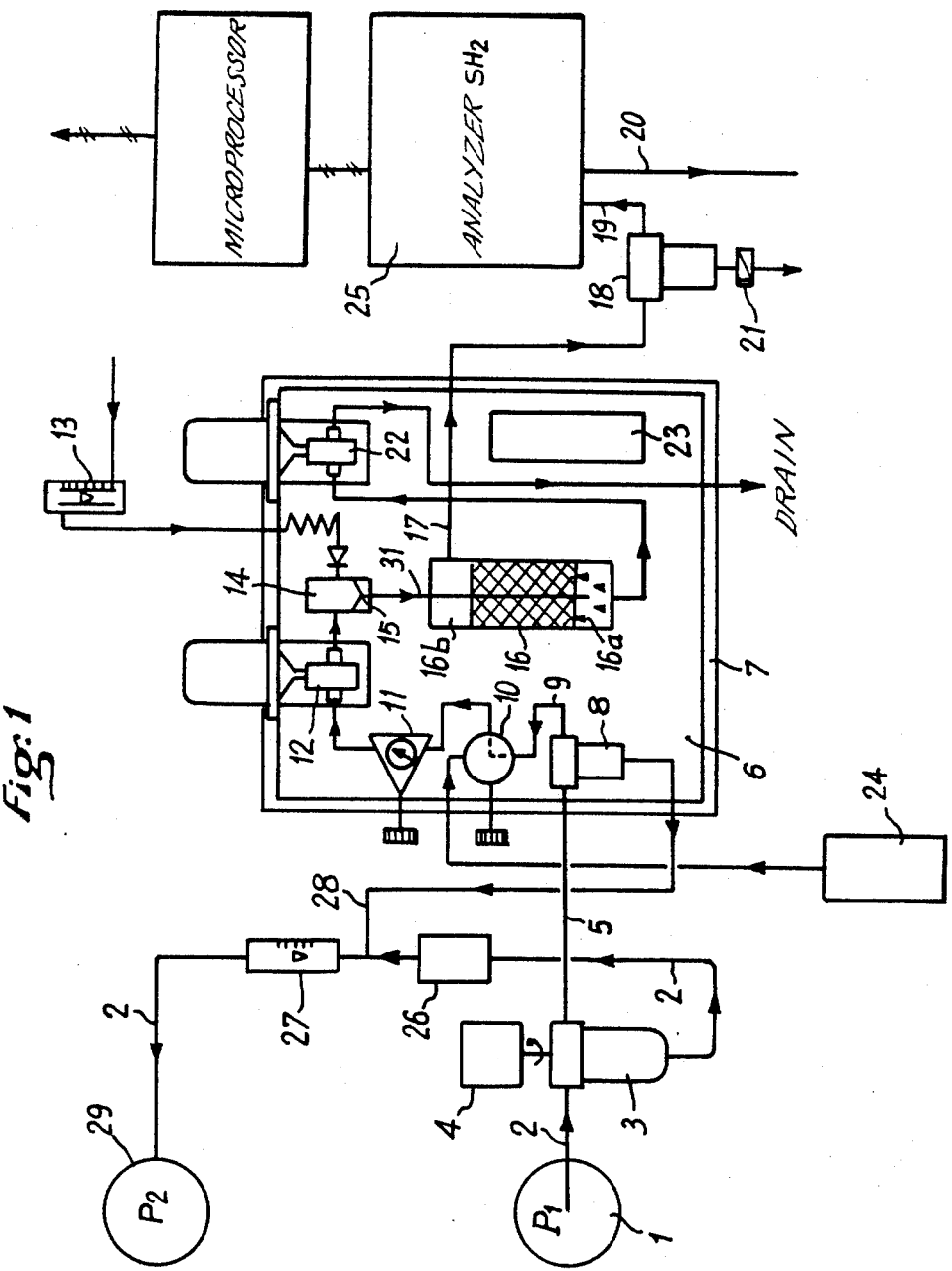
FIG. 1 shows the diagram of the first variant.

In the diagram shown in FIG. 1, oil whose $H_2S$ content is to be quantitatively analysed, at a pressure $P_1$ of 8 to 10 bars, is taken from duct 1 by means of a sampling loop tube 2 and fed to an automatic cleaning disk filter 3 whose scrapers are actuated by a pneumatic stepper motor 4.

The impurities and about 90% of the oil flow samples are conveyed by tube 2 of this loop through a flow rate regulator 26 and a flow indicator 27 to a duct 29 whose pressure $P_2$ is from 1 to 2 bars.

The filtered liquid is fed by a secondary sampling loop 5 to a thermostat controlled enclosure 6 with heat insulation 7 in which a pulsed air regulation block 23 maintains a uniform temperature of the order of 40° to 70° C. Flowing through a cartridge flow filter 8, the purified liquid is fed by a microtube 9 having a diameter of 1 mm through a three way microvalve 10 to a pressure reducer 11 regulating its pressure to a constant value, whereas the impurities collected in filter 8 return to loop 2 by tube 28. The three way microvalve 10 also serves for subjecting to analysis a reference sample coming from a pressurized oil reservoir 24.

The displacement micropump 12, with a rotary and reciprocating piston having valves cooperating with the intake port and discharge port of the cylinder, delivers a strictly controlled oil flow of the order of 1 cm$^3$/min into a mixing chamber 14 also receiving a stream of nitrogen at a constant regulated pressure coming from a flow rate regulator 13. The injection of the oil into the nitrogen stream in the mixing chamber 14 takes place through a calibrated orifice 15 of 0.5 to 0.7 mm in diameter and allows microspraying of the oil giving a mist of very fine droplets having a very large transfer surface. The mist is transported by duct 31 passing from top to bottom through a tower or chamber 16 to the lower part 16a of this chamber.

The tower 16 is filled in its central part with an aerosol or mist separation material formed by stacked layers of woven monofilaments, whereas its upper and lower parts are free of filling material. The mist arriving in zone 16a arrives in a rest chamber, where extraction and passage of droplets of $H_2S$ to the gaseous nitrogen phase take place. From chamber 16a, the mist rises over the whole section of chamber 16 through the stack of woven material and gives up its droplets which, coalesced, fall back to he bottom of the chamber. The gas free oil thus collected is discharged by means of a pump 22. In the upper part 16b of the chamber, only the $N_2$ and $H_2S$ mixture emerges and it is conveyed by duct 17 out of the thermostat controlled enclosure 6 towards a second coalescer 18, where, because of the ambient temperature at which it is placed, the rest of the light oil constituents are separated which are drained off with a larger part of the gas flow to the outside through valve 21.

The smallest part of the flow is conveyed by tube 19 to an $H_2S$ analyzer 25 where the $H_2S$ initially contained in the sampled oil is quantitatively analysed and then out through tube 20.

Figure 2:
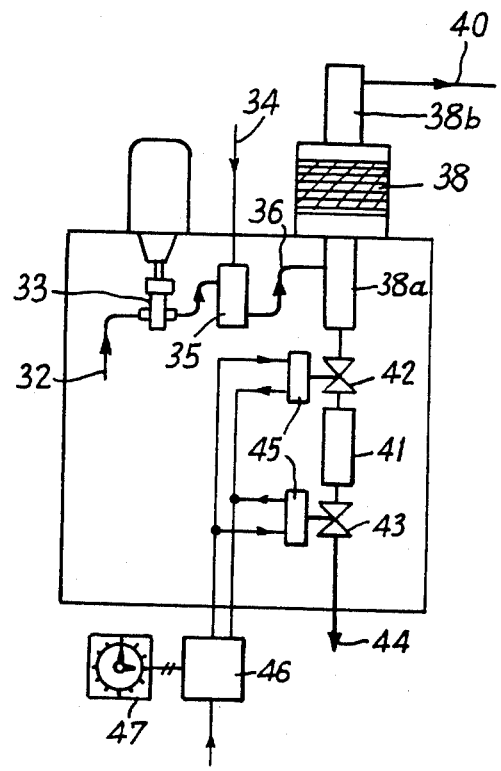
FIG. 2 a diagram of another variant.

In the variant shown in FIG. 2, the filtered and expanded sample arrives through 32 and reaches the displacement micropump 33, then is transformed into a mist in the mixing chamber 35 where it meets a nitrogen stream 34. The mist is conveyed to the mist separation chamber through tube 36 and then out of the mist separation chamber through tube 40.

The thermostat controlled enclosure shown contains the same elements as those shown in FIG. 1, except for the fact that the mist separation chamber 38 is formed of a lower part 38a placed inside the enclosure, of a central part filled with mist separation material placed outside the enclosure and having thereover an upper part 38b cooled to a temperature between $+5°$ and $+10°$ C. Since the nitrogen and $H_2S$ mixture contains practically no light hydrocarbons, whose elimination in the coalescer 18 of FIG. 1 was necessary, it may be fed directly to the analyzer.

The coalesced oil is collected at the lower part 38a, then passes through a drainage lock chamber formed by a capacity 41 placed between two valves 42 and 43 actuated in turn by double acting pneumatic servo motors 45 supplied by compressed air bottles 46 and controlled by a clockwork mechanism 47 and leaves the enclosure at 44.

The method of the invention is not limited to the examples described and may take on numerous embodiments within the scope of a man versed in the art.

I claim:

1. In a method of continuously preparing gas samples from a liquid in which said gas is initially dissolved, comprising filtering the liquid so as to free it of heavy constituents and impurities, expanding the liquid to a predetermined pressure, injecting a predetermined volume of the liquid into a nitrogen stream to form a sample, and conveying the sample thus prepared to a gas analyzer, the improvement which comprises injecting the predetermined volume of liquid into the nitrogen stream by injecting the nitrogen stream and the predetermined volume of liquid into a mixing chamber such that the predetermined volume of liquid is in the form of a microsprayed mist which meets the nitrogen stream and is conveyed thereby, and injecting the mist conveyed by the nitrogen into a mist separation chamber having a lower unfilled part, a top part, and a main body part which is filled with a solid mist separating material such that it enters the unfilled part, passes from bottom to top through said separating material and gives up liquid in the form of coalesced droplets on its way through the separating material and such that gas initially contained in the liquid and nitrogen emerge at the top part of the mist separation chamber free of at least a large part of the least volatile constituents of the liquid.

2. The method according to claim 1, wherein the predetermined volume of liquid is quantitatively obtained and delivered to said mixture by means of a displacement micropump operating in accordance with the principle of a rotating piston which moves with a reciprocating and translating movement inside a cylinder having liquid intake and discharge ports, said piston operating as a valve with respect to said ports so as to quantitatively obtain and deliver the predetermined volume of liquid to said mixing chamber.

3. The method according to claim 1, wherein the mixing chamber is connected to the mist separation chamber by a tube through which the mist conveyed by the nitrogen stream is brought to the lower part of the separation chamber while passing through the mist separating material in said separation chamber.

4. The method according to any one of claims 1 to 3, wherein the liquid is oil, the mist separation chamber is placed in a thermostat controlled enclosure whose temperature is kept between 40° and 70° C., and gas emerging from the top part of the separation chamber is conveyed by a tube out of the enclosure and passes through a second mist separation chamber at ambient temperature.

5. The method according to any one of claims 1 to 2, wherein the liquid is oil, the lower unfilled part of the separation chamber is placed in a thermostat controlled enclosure, the main body part of the separation chamber is placed at ambient temperature outside the thermostat controlled enclosure, and the top part of the separation chamber is in the form of an enclosure cooled to a temperature from 5° to 10° C. so that constituents of the mist leaving the mist separating material and having a condensation point greater than or equal to ambient temperature are condensed and fall by gravity back into said separating material.

6. The method according to claim 5, wherein coalesced oil droplets leave the separation chamber by gravity through a duct placed in the thermostat controlled enclosure and pass through a drainage lock chamber formed by two valves which have a capacity placed therebetween and which are actuated in turn by double acting pneumatic servo motors controlled by a clockwork mechanism.

* * * * *